US009585381B2

(12) United States Patent
Descargues

(10) Patent No.: US 9,585,381 B2
(45) Date of Patent: Mar. 7, 2017

(54) SYSTEM FOR KEEPING ALIVE AND TRANSPORTING SKIN BIOPSIES AND APPLICATIONS OF SAID SYSTEM

(71) Applicant: GENOSKIN, Toulouse (FR)

(72) Inventor: Pascal Descargues, Toulouse (FR)

(73) Assignee: GENOSKIN, Toulouse (FR)

( * ) Notice: Subject to any disclaimer, the term of this patent is extended or adjusted under 35 U.S.C. 154(b) by 18 days.

(21) Appl. No.: 14/398,587

(22) PCT Filed: May 3, 2013

(86) PCT No.: PCT/EP2013/059215
§ 371 (c)(1),
(2) Date: Nov. 3, 2014

(87) PCT Pub. No.: WO2013/164436
PCT Pub. Date: Nov. 7, 2013

(65) Prior Publication Data
US 2015/0132737 A1    May 14, 2015

(30) Foreign Application Priority Data

May 3, 2012  (FR) ..................................... 12 54091

(51) Int. Cl.
*A01N 1/02* (2006.01)
*G01N 33/50* (2006.01)

(52) U.S. Cl.
CPC ......... *A01N 1/0226* (2013.01); *A01N 1/0231* (2013.01); *G01N 33/502* (2013.01); *G01N 33/5044* (2013.01); *G01N 33/5082* (2013.01); *G01N 2500/10* (2013.01)

(58) Field of Classification Search
None
See application file for complete search history.

(56) References Cited

U.S. PATENT DOCUMENTS

| 2001/0049140 | A1* | 12/2001 | Baust ................ A01N 1/02 435/374 |
| 2003/0040113 | A1  | 2/2003  | Mizuno et al. |
| 2009/0145087 | A1* | 6/2009  | Allen-Hoffmann ...... A01N 1/02 53/440 |
| 2011/0045477 | A1  | 2/2011  | Chen et al. |

FOREIGN PATENT DOCUMENTS

| EP | 0 702 081 A2 | 3/1996 | |
| EP | 2 019 316 A2 | 1/2009 | |
| ES | WO 2011023843 A2 * | 3/2011 | ............. A61K 35/36 |
| ES | EP 2471902 A2 * | 7/2012 | ............. A61K 35/36 |
| WO | 2004/022696 A2 | 3/2004 | |
| WO | 2004/092354 A2 | 10/2004 | |
| WO | 2012/059703 A1 | 5/2012 | |

OTHER PUBLICATIONS

Mano et al. "Natural origin biodegradable systems in tissue engineering and regenerative medicine: present status and some moving trends", Journal of the Royal Society Interface 4: 999-1030, 2007.*
Collins et al. "Development of an in vitro organ culture model to study transmission of HIV-1 in the female genital tract", Nature Medicine 6(4): 475-479, 2000.*
Schafer et al. "Ascorbic acid deficiency in cultured human fibroblasts", The Journal of Cell Biology 34(1): 83-95, 1967.*
Huang et al. "Effect of calcium ion concentration on keratinocyte behaviors in the defined media", Biomedical Engineering—Application, Basis & Communications 18(1): 37-41, 2006.*
Holland et al. "Microbial colonization of an in vitro model of a tissue engineered human skin equivalent—a novel approach." FEMS Microbiology Letters 279(1): 110-115, 2008.*
Parsi et al. "In vitro effects of detergent sclerosants on clot formation and fibrinolysis." European Journal of Vascular and Endovascular Surgery 41(2): 267-277, 2011.*
Free Online Dictionary, definition for nacelle, available online << http://www.thefreedictionary.com/>>, accessed Jul. 8, 2016.*
Jacobs J J L et al.: "Methyl Green-Ypronine Staining of Porcine Organotypic Skin Explant Cultures: An Alternative Model for Screening for Skin Irritants", ATLA. Alternatives to Laboratory Animals, London, GB, vol. 28, Jan. 1, 2000 (Jan. 1, 2000), pp. 279-292, XP009038188, ISSN: 0261-1929 p. 280-p. 283.
Lebonvallet N et al: "The evolution and use of skin explants: potential and limitations for dermatological research", European Journal of Dermatology. John Libbey Eurotext, FR, vol. 20, No. 6. Nov. 1, 2010 (Nov. 1, 2010). pp. 1-14, XP009141240, ISSN: 1167-1122 [retrieved on Sep. 7, 2010] p. 1-p. 3.
Kishi K et al: "Treatment of giant congenital melanocytic nevi with enzymatically separated epidermal sheet grafting", Journal of Plastic. Reconstructive and Aesthetic Surgery. Churchill Livingstone. GB, vol. 63. No. 6. Jun. 1, 2010 (Jun. 1, 2010), pp. 914-920. XP002626328, ISSN: 1748-6815. DOI: 10.1016/J.BJPS.2009.03. 010 [retrieved on Apr. 26, 2009] p. 914-p. 916.
International Search Report, dated Jul. 8, 2013, from corresponding PCT application.

* cited by examiner

*Primary Examiner* — Emily Cordas
(74) *Attorney, Agent, or Firm* — Young & Thompson

(57) ABSTRACT

Disclosed is an in vitro or ex vivo method for preserving and/or keeping alive mammalian, preferably human skin biopsies, enabling to transport it and, if applicable, to culture it. Also disclosed is a skin biopsy thus preserved and obtained by such a method and relates to its use as a model especially in a kit for screening or selecting cosmetic or therapeutic compounds.

21 Claims, 2 Drawing Sheets

SYSTEM FOR KEEPING ALIVE AND TRANSPORTING SKIN BIOPSIES AND APPLICATIONS OF SAID SYSTEM

BACKGROUND OF THE INVENTION

Field of the Invention

The present invention relates to an in vitro or ex vivo method for preserving and/or keeping alive mammalian, preferably human skin biopsies, enabling to transport it and, if applicable, to culture it. The present invention also comprises a skin biopsy thus preserved and obtained by such a method and relates to its use as a model especially in a kit for screening or selecting cosmetic or therapeutic compounds.

Description of the Related Art

Skin is composed of the superimposition of epidermis and dermis. The epidermis is a stratified multi-layered and squamous epithelium. It forms a barrier which can withstand the damage of desiccation, as well as mechanical, chemical and microbial aggressions. The main cell type forming the epidermis is the keratinocyte. This tissues also comprises other cell populations such as the melanocytes, the Langerhans cells and the Merkel cells (see appendix). The epidermis is conventionally sub-divided into four distinct strata comprising internal layers towards the most superficial layers: the basal layer (a layer), the spinous layer (4-15 layers), the granular layer (1-3 layers) and the thorny layer (5-10 layers). The epidermis rests on the dermis thanks to a basal membrane formed among other things of collagen molecules. The dermis contains very dense vascular and nervous networks as well as the epidermal appendices, keratinised structures extending the epidermis and including the pilous follicles, the sebaceous glands and the sweat glands. The skin rests on a sub-cutaneous tissue, called hypodermis, mainly composed of fat cells playing a part, among other things in the elasticity of the skin and the thermoregulation of the system.

In vitro or ex vivo skin culture systems have long been developed for the academic or applied research (Lebonvallet et al. « The evolution and use of skin explants: potential and limitations for dermatological research." Eur J Dermatol 2010; 20 (6): 671-84). First of all, the ban of animal use for the development of cosmetic products in Europe (Pauwel M and Rogiers V. « Human health safety evaluation of cosmetics in the EU: a legally imposed challenge to science. » Toxicol Appl Pharmacol. 2010 Mar. 1; 243(2): 260-74), as well as the growing importance of the 3R-rule (Reducing, Replacing, Diminishing) relating to animal experimentation during pharmaceutical development (Wells D J. « Animal welfare and the 3Rs in European biomedical research. » Ann N Y Acad Sci. 2011 December; 1245:14-6), confer to in vitro or ex vivo skin culture systems, in particular those enabling human skin culture, a strategic importance for cosmetic, chemical and pharmaceutical industries. In vitro or ex vivo skin culture systems are ideal models for the study of cutaneous biology. Indeed, they possess all the cell types of the skin, organised into a 3D structure. They reflect directly the parameters of the individuals, such as the age, the sex, the pathological state of the skin or sun exposure (Lebonvallet et al., 2010).

If the in vitro or ex vivo culture systems or devices are ideal models for research, the existing systems or devices are ill-suited for transporting them or for keeping them alive.

Several, more or less perfected culture systems or devices exist (Lebonvallet et al., 2010), however these systems or devices are generally fragile and cannot be shipped by road or plane while maintaining their integrity. Indeed, in these systems or devices, the skin biopsy is not held firmly by a physical support. It can be left to float in a cultivation medium solution or laid on an insert with a porous membrane or a stainless steel grid. The advantage of the last two methods is that the superficial part of the epidermis, the thorny layer, is kept directly in contact with the atmospheric air. This enables to study the topical application of substance at the surface of the skin.

We may also mention here the patent documents published under the numbers EP 2 019 316, US2011/045477, or WO2004/092354 which describe in vitro or ex vivo skin culture systems, but which do not contain any support or device for maintaining or transporting skin biopsies.

More recently, a stainless steel chamber system has been developed for holding firmly large skin biopsies and enable the in vitro or ex vivo culture up to four weeks (Lars Steinstraesser et al. « A Human Full-Skin Culture System for Interventional Studies." Eplasty. 2009; 9: e5.). It may well be interesting enough, but this system is hardly suited for cell due to its dimensions and its composition (stainless steel). Moreover, this system is based on significant tensioning of the skin which does not reflect the physiological conditions encountered for this in vivo organ. EP 0 702 081 may also be quoted which describes a skin model comprising two types of collagen sponges of different density, Inoculated with fibroblasts and keratinocytes. This model can be placed in the centre of a well and surrounded with clotable gelatin. The publication of Jacobs et al. (« Methyl green-pyronine staining of porcins organotypic skin explant cultures: an alternative model for screening for skin irritants » , ATLA, 28,279-92, 2000) describes the use of pig skin biopsies placed in a culture medium, treated with an irritant, then included in a solid matrix, before being frozen and coloured. US 2003/040113 describes a multi-layered support for cell culture, in which the cell support is seeded with living cells suspended in a gel. WO 2004/022696 describes a fibrin support, comprising fibrinogen and thrombin, used for cell culture, especially keratinocytes. Finally, WO 2012/059703, filed before the present application and published on 10 May 2012, i.e. after filing the present application, describes a method for preserving and/or keeping alive the epidermis.

These documents do not divulge nor suggest a method for keeping alive and transporting a skin fragment or biopsy laid in a liquid matrix which is capable of solidifying, and hence held firmly by the matrix but also nourished, whereas the assembly is contained in an insert whose bottom is formed of a porous membrane.

As regards skin biopsies, the study of certain culture media used for keeping alive in vitro or ex vivo these skin biopsies have emphasised the deleterious effect of the presence of serum on the structure of the skin, whereas the presence of calcium at a concentration of 1.4 mM is important for the cohesion of the tissue via the stimulation of the production of extracellular matrix and of the epidermal differentiation (Lebonvallet et al., 2010).

For many years, we have sought to develop new methods so as to be able to preserve and/or keep alive mammalian, preferably human or pig, skin biopsies. All the more so since these methods enable transport and culture of these biopsies.

The development of such models is indeed quite important for dermatological research and for the studies necessary to the preparation of pharmaceutical and/or cosmetic products.

Thus, it would be desirable to have such a system, device and/or method available to obtain such skin biopsies, which are sufficiently heavy-duty to transport said biopsies (by air and/or by land).

Obtaining such a model would enable to preserve the 3D-organisation and the skin functions from a biopsy, and this advantageously with respect to the cultures of reconstructed skin, which normally take a long time to be developed and require complex techniques (whereas biopsies are easier to obtain and with a larger potential in terms of dermatological research, in particular for the studies on the extracellular matrix, 3D-structure or the interactions between the different types of cutaneous cells).

Such models would advantageously enable the realisation of studies necessary to better understanding of the role of the skin, especially of its epidermis and of the dermis, in the mechanical field as well as in the physiological field. Such biopsies, held firmly thanks to such as heavy-duty system, device and/or method, would also enable to sample cell layers from the thorny layer of the epidermis by successive superficial separations by tape stripping. Such biopsies, thus preserved and transportable, can also be used as ideal models, compared to the models of reconstructed skin and their shortcomings (see Lebonvallet et al., 2010) for predicting by in vitro or ex vivo tests, of the activity of cosmetic and/or pharmaceutical active principles or still of the secondary effects of topical compounds.

BRIEF SUMMARY OF THE INVENTION

Such is precisely the object of the present invention.

Surprisingly, the applicant has emphasised that the implementation of the method of the invention and of the device deriving therefrom as described hereafter enable to obtain skin biopsies which can be preserved and/or transported, and may be used, if applicable, as an experimentation model.

The object of the invention is therefore a method for ex vivo or in vitro keeping alive and for transporting a skin fragment or biopsy, whereas said skin fragment or biopsy has been taken previously from a mammalian, said method comprising the following steps:

a) Laying said skin fragment or biopsy on a liquid matrix so that the superficial part of said fragment or biopsy corresponding to at least 90%, preferably 95% or the whole epidermis remains emerged whereas the dermis underlying this epidermis is immersed at least by 90%, preferably 95% or totally, said liquid matrix being itself contained in an insert whose bottom is made of a porous membrane, and said insert being arranged in a container or well; and b) solidifying said matrix, whereas the purpose of said solidification is to trap the immersed portion of said skin fragment or biopsy in said matrix thus solidified, and to make said solidified matrix adhere to the lateral walls and to said porous membrane, and said epidermal superficial part of said fragment or of said biopsy remaining emerged, still in contact with the atmospheric air or under a controlled atmosphere partially comprising air.

Preferably, said insert is arranged in a container or an empty well (such a microplate or plate cupule which may be used for cell culture, preferably with a flat bottom).

In a particular embodiment, a method according to the invention includes, prior to laying the skin fragment or biopsy on a liquid matrix, a step of fixing to the epidermal surface of the fragment or of the biopsy a ring, or perforated disc, made of a water-repellent material, whereas the outer diameter of said ring is greater than the diameter of the epidermal surface of the fragment or of the biopsy, whereas the inner diameter of said ring is smaller than the diameter of the epidermal surface of the fragment or of the biopsy.

More precisely, the ring is fastened prior to step a) of laying the fragment, and prior to step i) of floating the garment or biopsy.

Preferably, the water-repellent material of the ring is a skin-harmless material, it may be a paraffin polymer, such as a Parafilm® (Sigma) or a silicon polymer. According to a particular mode, the ring is prepared from a film of water-repellent matter, by perforating said film according to the desired dimensions. The thickness of the ring is preferably comprised between 0.1 mm and 2 mm, preferably between 0.1 and 1 mm, more preferably between 0.1 and 0.5 mm, and even more preferably between 0.12 and 0.2 mm.

Said ring may be composed of an opaque or translucent material. According to a particular embodiment, the ring is formed by an opaque material.

According to a more particular embodiment, said ring is fixed to the epidermal surface of the fragment or of the biopsy using glue, whereas said glue is preferably added to the lower surface of the ring. Said glue can be selected among any type of skin-harmless material and causing the ring to adhere to the skin, whereas said material can be silicon. Preferably, said glue is water repellent.

Preferably after step b), said container or well is covered by a lid and, if applicable sealed and wrapped in a transportable protective envelope.

A liquid matrix capable of solidifying is a liquid solution comprising at least one specific compound or composition whose concentration in said liquid solution is such that, when implementing suitable conditions, especially particular temperature conditions, the liquid solution takes on a solid or jellified consistency. Said specific compound or composition may be of animal, vegetal or synthetic origin, its nature and its concentration are determined according to the desired physicochemical characteristics of the matrix when it is solidified, especially the flexibility and the resistance of the matrix.

In a preferred embodiment of the method according to the invention, in step a), said liquid solution capable of solidifying is selected among any liquid, preferably nutritive solution, capable of solidifying or jellifying under particular conditions compatible with the survival and the culture of the skin cells forming said fragment or biopsy, preferably selected among blood plasma or a solution derived from blood plasma, especially diluted as a physiological buffer by max. 10%, preferably at least 20%, at least 30% and 40%, a fibrinogen solution, a collagen solution, gelatin, synthetic polymeric gels, natural gels, such as agarose gels, in particular agarose or agar-agar gels with low melting points, starch or polysaccharide gels, or one of their mixtures.

In a particularly preferred aspect, the object of the present invention is an ex vivo or in vitro method for preserving or keeping alive a skin fragment or biopsy, said fragment or biopsy being transportable, said fragment or biopsy having been taken previously from a mammalian or obtained from a collection or a skin sample bank, or still from a cultured skin, characterised in that said method comprises the following steps:

i) floating a biopsy of cylindrical skin in a liquid matrix selected among a solution derived from blood plasma, a fibrinogen or collagen solution, or a low-melting agar-agar or agarose solution, or a mixture of these solutions, this liquid matrix being contained in said insert, said floating leaving the epidermal surface of the emerged biopsy, while the dermis is immersed;

ii) the rapid induction of the solidification of said matrix surrounding the skin biopsy; and, iii) in vitro or ex vivo culture, or keeping alive the skin fragment or biopsy in said matrix thus solidified.

Preferably, said liquid or solidified matrix does not contain any growth factor nor serum.

Preferably, in step i) the floating of a cylindrical skin fragment or biopsy is carried out in a liquid matrix comprising a first solution selected among a solution derived from blood plasma, a fibrinogen solution or a collagen solution, and a second, low-melting agar-agar or agarose solution.

When the liquid matrix contains a low-melting agar-agar or agarose solution, said second solution is previously heated for sufficient duration and at sufficient temperature to become liquid and stay liquid at 37° for the time sufficient to be mixed with the first solution in said insert and until said skin fragment or biopsy is laid.

Preferably, said second solution is previously heated at its melting temperature, or slightly higher, preferably between 65° C. and 70° C.

Preferably, low-melting agar-agar or agarose is an agar-agar or agarose whose maximum jellification temperature is comprises between 24° C. and 28° C., and the melting temperature is greater than 65.5° C. in a 1.5%-solution.

Preferably, and by way of example, without limitation thereto, said agarose is LMP agarose, for Low melting point agarose (GIBCOBRL, Life Technologies)

Preferably, said second solution is a low-melting agar-agar or agarose solution, wherein the concentration in low-melting agar-agar or agarose ranges between 1% and 5% (preferably in a physiological solution), more preferably ranging between 2% and 5%, between 3% and 4.5%, between 3.5% and 4.5% or still between 3.8% and 4.2% or between 3.9% and 4.1%, whereas 4% is the most preferred concentration.

This second low-melting agar-agar or agarose solution at said concentration and once heated to its melting temperature, or slightly higher, can be kept in liquid form for at least one hour and, preferably at least 4 hours, 10 hours or 16 hours at 37° C.

Preferably, in said liquid matrix comprising said first and second low-melting agar-agar or agarose solution, the final concentration in low-melting agar-agar or agarose ranges between 0.1% and 2%, preferably between 0.2% and 1.8%.

Such a concentration enables to obtain not only a matrix which once solidified enables to keep the 3D-structure and to keep alive said skin fragment or biopsy, but also to obtain such a solid and sufficiently flexible matrix that it is non-brittle and resistant to punctual shocks. Said liquid matrix is solidified after laying the skin fragment or biopsy by leaving the device thus obtained at a temperature comprised between 37° C. and the room temperature, preferably 20° C.

According to a particular embodiment, in said liquid matrix comprising said first and second low-melting agar-agar or agarose solution, the final concentration in low-melting agar-agar or agarose ranges between 1% and 2%, preferably between 1.25% and 1.75%, preferably between 1.4% and 1.6%, whereas 1.5% is the most preferred concentration.

According to another particular embodiment, in said liquid matrix comprising said first and second low-melting agar-agar or agarose solution, the final concentration in low-melting agar-agar or agarose ranges between 0.1% and 2%, preferably between 0.2% and 1.75%, whereas 0.25% is the most preferred concentration. Such a concentration enables to obtain not only a matrix which once solidified enables to keep the 3D-structure and to keep alive said skin fragment or biopsy, but also to obtain such a sufficiently flexible matrix that it is non-brittle and resistant to mechanical effects applied to the fragment or to the biopsy, for example during an effect mimicking the massage of the skin for the application of a preparation like, for instance, a cream. Said liquid matrix is solidified after laying the skin fragment or biopsy by leaving the device thus obtained at a temperature comprised between 37° C. and the room temperature, preferably 20° C.

Preferably, the volume of said liquid matrix corresponds to ⅓-⅔ of the total volume of the insert, preferably ⅖-⅗ of the total volume, half the total volume of the insert being the preferred volume.

Preferably, said liquid matrix capable of solidifying moreover contains other cells than the cells forming said skin fragment or biopsy, preferably selected in the group of cells formed by fibroblasts, endothelial cells or nervous cells.

In an even more preferred embodiment, said cells are fibroblasts, preferably primary fibroblasts (in opposition to fibroblasts lineages) preferably still dermal fibroblasts or obtained from human foreskins.

These primary, especially dermal fibroblasts can be prepared and obtained from standard methods well known to those skilled in the art (see for example the document Howard B V et al., A new method for the establishment of diploid fibroblast cell cultures from human foreskins. Proc Soc Exp Biol Med. 1976 November; 153(2):280-3).

Preferably, said cells, especially the fibroblasts are contained in the matrix at a concentration between $5 \cdot 10^3$ and $5 \cdot 10^5$ per ml, preferably still between $10^4$ and $10^5$ per ml, between $3 \cdot 10^4$ and $5 \cdot 10^4$ per ml being the most preferred concentration.

The method according to the invention as described both enables secure culturing and transport of skin biopsies (by land, sea or air). Indeed, the skin fragment or biopsy is not only trapped and hence held firmly by the solid matrix in the insert with a porous membrane, but also nourished, which may travel without a culture medium during transport while being kept alive.

By culture is meant here in particular keeping the physiological state and, if applicable, the morphological state of the skin explant, and therefore of said cells forming it.

This method can advantageously lay the skin fragment or biopsy in a first step on a liquid phase (by means especially of an insert containing said matrix in liquid form, a liquid matrix which may be solidified), and, in a second step, solidify said liquid matrix, which solidification enables to fix or freeze the 3D-structure of said fragment or biopsy, thereby enabling to preserve or keep alive such an explant and its possible transport while also maintaining its 3D-structure.

This method proves advantageous in that it enables to obtain a skin fragment or biopsy which can be preserved or kept alive over a long period without a noticeable degradation, which moreover can be transported, by land, sea or air.

Said skin fragment or biopsy will include preferably at least the epidermis, the dermis and the epidermal appendices.

Preferably, said epidermis includes all of its cell layers as well as the whole of the epidermal appendices.

By « all of its cell layers » for an epidermis are meant the basal layer, the spinous layer, the granular layer and the thorny layer.

By « the whole of the epidermal appendices » are meant the pilous follicles, the sebaceous glands and the sweat glands.

This skin fragment or biopsy may also include a portion of the subcutaneous tissue also called hypodermis.

Preferably still, said skin fragment or biopsy is a mammalian fragment or biopsy selected among man or pig.

Preferably also, said skin fragment or biopsy is freshly sampled to keep it alive in vitro or ex vivo.

By freshly sampled is meant here a sampling made less than an hour ago, preferably less than 24 hours.

The skin fragments or biopsies are prepared preferably from healthy skin, from any location of a mammalian body, such as for example but without limitation the abdomen, the chest, the breast (or udders), scalp, buttocks etc. . . . ).

The skin fragments or biopsies are prepared preferably also from mammalian skin exhibiting a pathology, such as for example but without limitation pathological tissues from exeresis, and taken from example from a patient or an animal with cutaneous cancer (melanoma, baso- or spino-cellular cancers, other of cutaneous cancer), a psoriasis plate, an eczema injury or an atopic dermatitis or any other type of cutaneous pathology.

Under a particular aspect, said skin fragment or biopsy used in this method is a skin fragment or biopsy from a collection or obtained after skin culture.

Preferably, skin fragments or biopsies are cylindrical in shape.

Preferably, the skin fragments or biopsies are cylindrical in shape whose diameter may vary between 1 mm and 50 mm, more preferably between 1 and 20 mm in diameter, preferably still between 1 and 10 mm.

According to an also preferred embodiment, said previously taken fragment is a cylindrical fragment whose thickness ranges between 1 and 20 mm, preferably between 2 and 15 mm in thickness, still preferably between 2 and 10 mm.

In a preferred embodiment, said insert whose bottom is made of a porous membrane is a nacelle-shaped insert, preferably whose diameter ranges between 5 and 40 mm, more preferably between 9.5 and 30 mm.

Preferably still, said insert is a suspended insert or on stilts, preferably suspended.

Preferably still, said porous membrane is a membrane with a porosity enabling to prevent the liquid matrix from flowing through the membrane before solidification, preferably still selected between 0.4 and 8 µm, more preferably still between 0.4 and 1.5 µm, whereas between 0.8 µm and 1.2 µm is the preferred porosity.

Preferably still, said porous membrane is a selected membrane of polyethylene terephthalate (PET), nitrocellulose or polycarbonate.

Among these inserts, we may quote those supplied in particular by Nunc (Roskilde, Danemark), BD Falcon (Becton Dickinson France SAS, 38801 Le Pont-De-Claix, France, Millicell® (EMD Millipore Corporation, Billerica, Mass., USA) ou Costar® (Grosseron SAS, 44819 Saint-Herblain France), for example the inserts with a membrane made of polycarbonate, PET or pre-packaged nitrocellulose in multi-well plates for 6, 8, 12 and 24-well Petri-boxes and where the porosity of the membrane may vary between 0.4 and 8 µm, where the 8-well boxes and/or with a membrane porosity of 0.8 µm to 1 µm and/or PET are the most preferred.

In a preferred embodiment, said container, in which said insert has been laid, is a well with a cell culture plate containing 6, 8, 12, 24 or 48 wells.

Among these culture plates, we may mention those supplied in particular by Nunc, BD Falcon or under the references Millicell® or Costar®.

Preferably, the bottom of the insert is situated at a distance ranging between 1 mm and 2.5 mm of the bottom of the contained including insert, especially of the bottom of the well of the culture plate (or of the bottom of the Petri bottom according to the designation).

In another preferred embodiment, in step a), said liquid matrix contains 1 mM and 5 mM of $Ca^{2+}$, preferably between 1.5 mM and 4.5 mM of $Ca^{2+}$. In another preferred embodiment, in step a), said liquid matrix contains 1 mM and 2 mM of $Ca^{2+}$, preferably between 1.2 mM and 1.4 mM of $Ca^{2+}$. In another preferred embodiment, in step a), said liquid matrix contains 2 mM and 3 mM of $Ca^{2+}$, preferably between 2.5 mM and 2.8 mM of $Ca^{2+}$ and more preferably 2.8 mM of Ca2+.

Preferably also, said liquid matrix contains between 5 and 500 mg/ml ascorbic acid, preferably between 25 and 75 mg/mL, whereas 50 mg/mL ascorbic acid is the most preferred concentration.

In a preferred embodiment, said liquid matrix contained in the insert in step a), is a liquid matrix, whose first solution of the mixture (whereas the second solution is the agar-agar or agarose solution) is preferably nutritive, and also capable of solidifying under the action of an increasing or decreasing temperature and/or the addition of a specific compound or composition.

Preferably, said liquid matrix does not contain any growth factor nor animal or human serum.

Preferably, in step a), said liquid matrix does not cover the upper face of the epidermis before said matrix is solidified in step b).

According to another also preferred embodiment, in step a) of said method, the skin fragment or biopsy is then placed on a liquid matrix capable of solidifying, especially as stated above, and which liquid matrix is selected among any liquid solution providing all the nutritive ingredients and/or necessary to its culture, in particular to maintain the initial physiological condition of the cells forming it. This solution is capable of solidifying or jellifying under particular conditions compatible with the survival and the culture of the skin fragment or biopsy.

Preferably, said liquid matrix is capable of solidifying is a liquid solution derived from a blood plasma treated with an anticoagulant agent with reversible properties, mixed with an agar-agar or agarose solution.

Preferably, said liquid matrix contains a blood plasma, fibrinogen or collagen, mixed with a low-melting agar-agar or agarose solution.

According to an also preferred embodiment of the method of the invention, in step a), said liquid matrix capable of solidifying is a solution derived from a blood plasma containing 25% to 60%, preferably between 35% and 45% (v/v) blood plasma, 70% to 35% of a physiological solution, such as a solution of NaCl at 0.9%, from 5% to 12%, preferably 8%, of a salt solution of $CaCl_2$ at 1%, of an anti-fibrinolytic agent in sufficient concentration to obtain the desired anti-fibrinolytic activity, preferably between 5% and 2%, whereas preferably the anti-fibrinolytic agent is selected among tranaxemix acid or aprotinin, and a low-melting agarose solution between 0.5% and 4%, preferably between 1% and 2%.

In an also preferred embodiment of the method according to the invention, in step a), said liquid matrix capable of solidifying is a fibrinogen and thrombin or collagen liquid or blood plasma solution, mixed with a gelatin solution, comprising synthetic polymeric gels, natural gels such as agarose gels, in particular agarose or agar-agar gels with low melting points, starch or polysaccharide gels and for which 37° C. incubation enables the solidification thereof.

In an also preferred embodiment of the method according to the invention, in step a), said liquid matrix capable of solidifying contains a liquid solution derived from a blood plasma treated with an anticoagulant agent with reversible properties, preferably with sodium citrate; and whereas solidification of said matrix in step b) for this solution can be obtained in the presence of calcium ions, preferably also in the presence of thrombin.

When the liquid matrix is a liquid matrix containing a blood plasma solution, a fibrinogen or collagen solution, the solidification of said matrix in step b) can be carried out for this solution by adding thrombin or by increasing the temperature, or still using factors secreted by cells brought to the matrix, such as primary fibroblasts.

In an also preferred embodiment of the method according to the invention, in step b), said liquid matrix is solidified after maximum 8 hours, preferably less than 2 hours or less than one hour, whereas a duration of less than 30 min, preferably of less than 10 min is the most preferred duration to initiate the solidification phase of the liquid matrix after laying the skin fragment or biopsy on said liquid matrix at step a).

Under another aspect, the invention relates to the use of such a skin fragment or biopsy obtained by such a method according to the present invention to provide ex vivo or in vivo models, in particular toxicological analyses, especially pertaining to percutaneous absorption, metabolism, Sensitisation, corrosion or irritation or for research purpose, in particular certain exogenous parameters such as UVs, stress, medications or active principles with a cosmetic effect, o still certain signalling proteins such as cytokines, could be applied on such models to study the responses of the cells and of the tissues forming the skin or associated thereto.

Preferably, said toxicological analyses are selected among the skin sensitisation, absorption, metabolism, corrosion or irritation tests.

Under another aspect, the object of the present invention is an ex vivo or in vitro method for preserving or keeping alive a skin fragment or biopsy which can be transported, said method comprising the following steps:

A) preserving or keeping alive a skin fragment or biopsy previously taken and capable of being transported, by a method according to the present invention;

B) transporting said skin fragment or biopsy thus obtained in step A); and

C) culturing said skin fragment or biopsy thus obtained after transport in step B) under adequate culture conditions and/or in the presence of the compound(s) to be tested, whereas the epidermis of said skin fragment or biopsy is in contact with air.

Preferably, in step C) culturing said skin fragment or biopsy thus obtained after transport in step B) under adequate culture conditions and/or in the presence of the compound(s) to be tested, can be carried out by means of an additional culture medium which may contain said compounds, and added in the container or well, whereas this additional medium can diffuse through the porous membrane of the insert.

In an also preferred embodiment of the method according to the invention, in step C), said skin fragment or biopsy thus laid is cultivated for a period between 1 and 15 days and preferably between 1 and 7 days, and at a temperature ranging 4° C. and 37° C.

In another aspect, the object of the invention is a device for preserving and/or keeping alive a skin fragment or biopsy comprising an insert whose bottom is made of a porous membrane, said insert being laid in a well, and said insert containing a liquid matrix capable of solidifying or jellifying.

According to another aspect, the object of the invention is a device for preserving and/or keeping alive a skin fragment or biopsy comprising an insert whose bottom is made of a porous membrane, said insert being laid in a well, and said insert containing a solidified or jellified matrix adhering to the side walls and to the said porous membrane of the insert.

In a device according to the invention, said insert is arranged in a container or an empty well, such a microplate or plate cupule which may be used for cell culture, preferably with a flat bottom. Preferably, said insert is suspended in the contained or the well and can be removed from the contained or from the well.

In a particular embodiment of a device according to the invention, said liquid matrix which is capable of solidifying, or said solidified or jellified matrix adhering to the side walls and to said porous membrane of the insert, is selected among any liquid, preferably nutritive solution, capable of solidifying or jellifying under particular conditions compatible with the survival and the culture of the skin fragment or biopsy forming said fragment or biopsy, Preferably selected among blood plasma or a solution derived from a blood plasma, especially diluted in a physiological buffer with maximum 10%, preferably at least 20%, at least 30% and 40% concentration, a fibrinogen solution, a collagen solution, gelatin, synthetic polymeric gels, natural gels such as agarose gels, in particular agarose or agar-agar gels with low melting points, starch or polysaccharide gels or one of their mixtures.

Preferably, said matrix contains a solution derived from blood plasma, a fibrinogen or collagen solution, a low-melting agar-agar or agarose solution, or a mixture of these solutions.

Preferably, in said liquid matrix comprising said first and said second low-melting agar-agar or agarose solution, the final concentration in low-melting agar-agar or agarose ranges between 0.1% and 2%, preferably between 0.2% and 1.8%.

According to a particular embodiment, in said liquid matrix comprising said first and said second low-melting agar-agar or agarose solution, the final concentration in low-melting agar-agar or agarose ranges between 1% and 2%, preferably between 1.25% and 1.75%, preferably between 1.4% and 1.6%, whereas 1.5% is the most preferred concentration.

According to another particular embodiment, in said liquid matrix comprising said first and said second low-melting agar-agar or agarose solution, the final concentration in low-melting agar-agar or agarose ranges between 0.1% and 2%, preferably between 0.2% and 1.75%, whereas 0.25% is the most preferred concentration.

Preferably, the floating of a skin biopsy or fragment in a matrix of a device according to the invention leaves the epidermal surface emerged while the dermis is immersed.

In another aspect, the object of the present invention is a skin fragment or biopsy which can be obtained or is obtained directly by the method of the present invention, as a model.

This aspect of the invention also provides a kit comprising such a skin fragment or biopsy as a model, whereas said kit requires the presence of a solid matrix, Said solid matrix being adapted by its composition for preserving and/or keeping alive the structure, in particular the 3D-structure, of said skin, as well as for transporting it.

Thus, according to this aspect, the invention also relates to a kit, in particular for assessing or for selecting a cosmetic, dermatological or therapeutical compound for the skin, including such a skin fragment or biopsy as a skin model and obtained according to the method of the invention.

Another object of the present invention relates to an in vitro screening method of candidate compounds for the cosmetic or therapeutic treatment of the skin, whereas this method comprises the following steps:

a) obtaining a skin fragment or biopsy as a model according to the present invention;

b) contacting said model with the candidate compound; and c) highlighting a physiological modification; and d) selecting said compound if the modifications obtained are those requested for the treatment.

Another object of this invention relates to a method for taking successive samples of superficial cellular layers using adhesives (so-called "tape-stripping"), characterised in that said samplings are taken from a model of skin biopsy or fragment obtained by the method of the invention. These cellular layers can be analysed independently from the whole biopsy.

Thus the skin fragment or biopsy as a model according to the invention can be used in any method, especially an automated method, for screening or identifying new cosmetic, dermatological or pharmaceutical compounds intended in particular for skin application.

The screening methods provided for identifying new efficient compounds generally comprise contacting said compound to be tested with a skin model obtained according to the invention then a step of reading the effect of the compound on said model, especially by comparing said effect with a control or reference model according to the invention which has not been contacted with the compound to be tested. This last reading step may also be realised by the determination or the analysis of epidermal markers and/or associated cells and included in the solidified matrix, such as proteins associated with these structures. For example, if these associated cells are immune system cells, said screening method will be for instance intended for identifying or selecting test compounds which may induce undesirable secondary effects, such as allergic or sensitisation reactions.

The products tested can also be gene expression vectors or still nucleic acids, such as antisense, microRNA, siRNA nucleic acids, which can modify the gene constitutive of cells present in said model of the invention.

Other effects such as the expression of certain mediators or the intrinsic cytotoxicity of the test compounds as regards certain skin cells may also be investigated as a secondary effect, or as regards certain associated cells which might have been inserted moreover with the skin biopsy into the matrix before solidification.

These references models will obviously be implemented under the same conditions as a model of the invention having received the product to be tested.

Under another aspect, the present invention relates to a method to determine the suitable therapeutic treatment for an individual suffering from a skin disorder or pathology, in particular, in the epidermis or the dermis, whereas said method comprises the following steps:

a) from a skin fragment taken from said patient, obtaining a model according to the present invention;

b) contacting said model with a candidate compound for said treatment;

c) highlighting any physiological or morphogenic modification of the skin, in particular of the epidermis or of the dermis, associated with the efficient treatment for said disorder or said pathology;

d) selecting said compound if the modifications obtained are those requested for the treatment.

In another aspect, the present invention relates to a method to determine the suitable therapeutic treatment for an individual suffering from a skin disorder, in particular, in the epidermis or the dermis, according to the present invention, Characterised in that in step a), the skin fragment or biopsy used is a fragment derived from a skin collection or culture.

In another aspect, the object of the present invention is the use of a model according to the present invention, to determine for a product the secondary effects on the skin such as for example:

its toxicity;

its adsorption or absorption;

its distribution, its metabolism, its excretion;

its irritating or corrosive power;

its sensitising power.

Such a model may be indeed according to the present invention be used or implemented in any in vitro or ex vivo method or test requiring animal or human experiments, Such as for instance the study of the release or of the penetration of active principles and/or of their cutaneous bioavailability, the study of their efficiency or still of their Tolerance, of their compatibility, whereas said active principles are intended for cosmetic, dermatological and/or pharmaceutical purposes.

According to a preferred embodiment, said product tests is a cosmetic, dermatological or pharmaceutical product.

The use as a model will also relate to its implementation for the study of any pathology reflecting by skin anomalies, especially of the epidermis and/or of the dermis, in particular also for all the cells situated under the epidermis for which the epidermis forms a natural barrier and for which a therapy by topical route can be envisioned.

BRIEF DESCRIPTION OF THE DRAWINGS

Other characteristics and advantages of the invention appear in the next section of the description with the example and the figures. The figures whose captions are listed below, as well as the following examples are intended for illustrating the invention without limiting the scope thereof.

CAPTION OF FIGURES

Figure 1A:
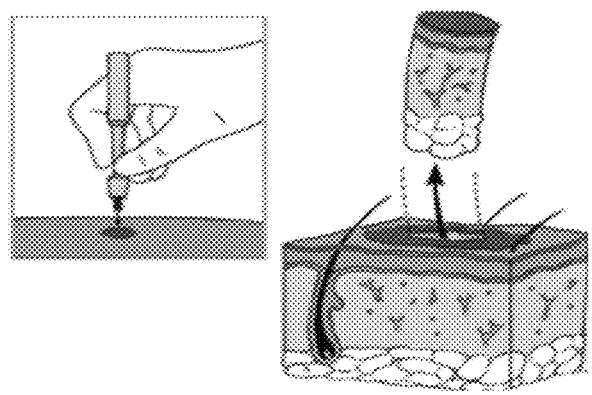
Figure 1B:
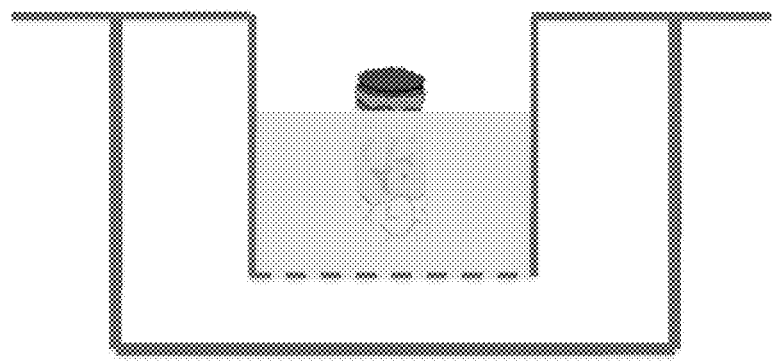
Figure 1C:
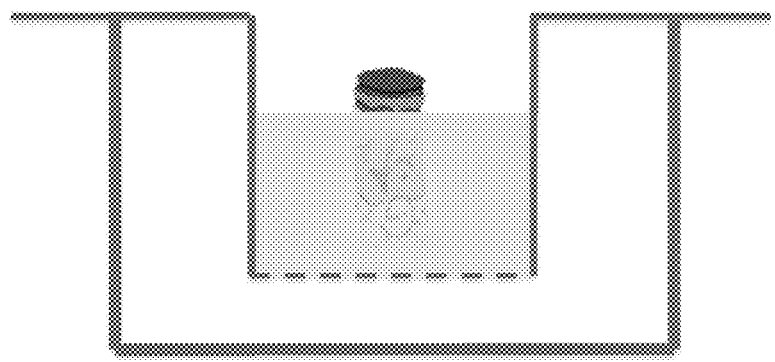

FIGS. 1A, 1B and 1C: Diagram describing the method according to the invention

Step 1: A cylindrical skin biopsy is carried out (FIG. 1A);

Step 2: The biopsy is floated in a contained/insert with a porous membrane containing a solution prepared with a mixture of blood plasma and melted agarose, Whereas insert is itself arranged (suspended) in a cellular culture plate well which has not been pre-filled with a nutritive medium (FIG. 1B);

Step 3: The blood plasma solution is solidified by coagulation; and the biopsy laid on the coagulated plasma is kept in culture thanks to the diffusion of the culture medium through the porous membrane of the insert (FIG. 1C).

Figure 2:
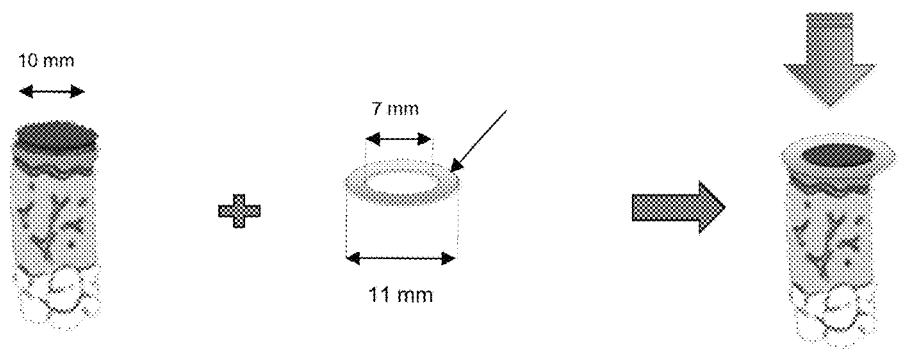

FIG. 2: Diagram describing the fastening of the water repellent ring on the epidermal surface of the biopsy.

Figure 3A:
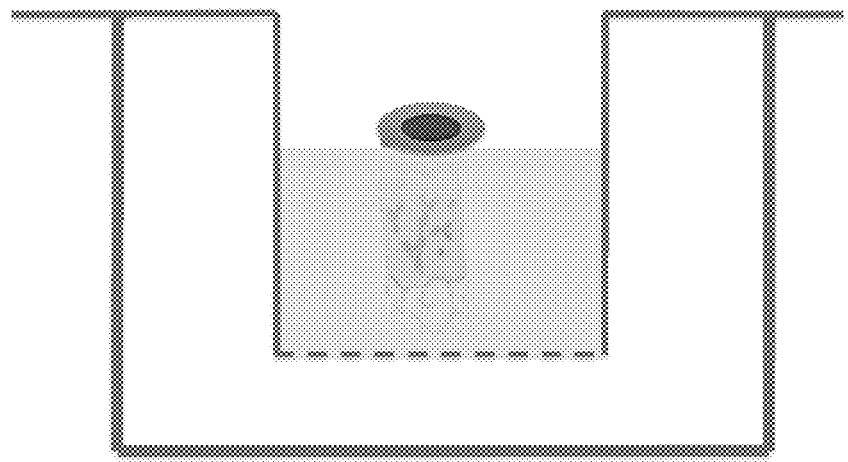
Figure 3B:
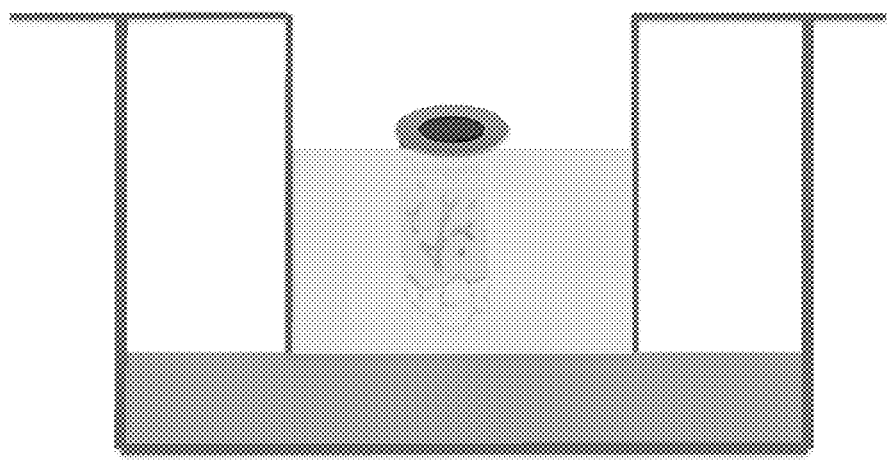

FIGS. 3A and 3B: Diagram representing the biopsy associated with the ring, floated in an insert with a porous membrane containing the matrix, in which the cellular culture well is not pre-filled with a nutritive medium (FIG. 3A) or in which the cellular culture well is filled with a nutritive medium (FIG. 3B).

DETAILED DESCRIPTION OF THE PREFERRED EMBODIMENTS

Example 1

Implementation of the Method (see FIGS. 1A, 1B and 1C)

A device for preserving and/or keeping alive a skin fragment or biopsy comprising an insert whose bottom is made of a porous membrane. The insert contains a liquid matrix capable of solidifying or jellifying, the insert is laid in a well.

1. A cylindrical skin biopsy (8 mm diameter, 5 mm thickness) is first of all realised on a skin fragment freshly sampled for easier ex vivo or in vitro survival.

2. The biopsy is laid delicately in an insert (Millicell™ 8-well cupule) with a porous membrane (made of PET, 1 μm porosity) at the bottom, said insert containing a solution derived from a blood plasma treated with an anticoagulant agent with reversible properties in the presence of calcium ions (sodium citrate). This solution contains 42% blood plasma, 50% of a solution of NaCl at 0.9%, 8% of a salt solution of CaCl2 at 1%, an anti-fibrinolytic agent (tranaxemic acid or aprotinin) and of low-melting melted agarose at 1.5% (Agarose LMP GIBCOBRL, Life Technologies) (melted in a stove at 65.5° C.).

3. By coagulating, the plasma acts as a dermal support on which the skin explant adheres. The coagulation mainly consists of the transformation, in the presence of calcium ions and of thrombin, of the fibrinogen present in the plasma into a scaffolding of fibrin molecules linked together by covalent bonds. The function of the anti-fibrinolytic agent is to inhibit the enzymes capable of degrading the plasma matrix, whereas said enzymes are secreted by the skin explant, and thus to maintain the integrity of the explant. Similarly, the plasma solution can be substituted with a fibrinogen or collagen solution. For the latter, only incubation at 37° C. permits solidification.

4. The 1.5%-agarose solution contained in the plasma solution gradually jellifies at 37° C. thereby permitting to hold firmly the skin biopsy in the insert. The skin biopsy can thus be transported without alteration for a duration of 24 h, 48 h or more, to suit the needs.

5. The whole constituted by the skin explant (or still called here skin fragment or biopsy) is kept in culture with the epidermis in contact with the air and the nutritive medium contained in the insert laid (suspended) on the well of the cellular culture plate. In case of need, the mobile insert can be lifted, thereby permitting the addition or the renewal of a nutritive medium in the well, or the addition of a particular additive to the nutritive medium. In a particular embodiment, Said additive is a compound intended for testing when in contact with the fragment or the biopsy.

The presence of a porous membrane whose bottom of the insert enables the diffusion of the nutritive elements through the membrane, and if needed, the diffusion of compounds produced by the skin fragment or biopsy during culture, and whereas the local accumulation thereof could be damaging for said fragment or biopsy.

Example 2

Implementation of the Method in which a Water Repellent Ring is Fixed to the Biopsy A ring, or perforated disc, whose inner diameter is 7 mm and the outer diameter is 11 mm, is cut in a water repellent film of Parafilm® (Sigma) type which thickness ranges between 100 and 120 Microns. A cylindrical skin biopsy (10 mm diameter) is realised on a skin fragment freshly sampled for easier ex vivo or in vitro survival. The lower face of the ring is coated with liquid silicon, which enables the adhesion of the ring to the biopsy. The ring is pressed onto the epidermal surface of the biopsy, so that it overlaps the surface of the biopsy (FIG. 2). The disc is arranged so that its centre matches that of the biopsy. The assembly constituted by the biopsy and the water repellent ring is delicately laid on an insert (Millicell™ hanging inserts, Merck Millipore) at the bottom of a porous membrane (made of PET, 1 μm porosity), whereas this insert contains a solution derived from a blood plasma as described in the example 1. In this case, only incubation at 37° C. permits solidification, the 1.5%-agarose solution contained in the plasma solution gradually jellifies at 37° C. thereby permitting to hold firmly the skin biopsy in the insert (FIG. 3A). The assembly constituted by the biopsy and the water repellent is kept in culture, with the epidermis in contact with air, in contact with the nutritive medium contained in the well of the cellular culture plate in which the insert is laid (FIG. 3B).

In a particular example, the presence of a water repellent ring delineating a 0.5 cm² area enables to lay and to hold in contact with the biopsy, a volume of liquid solution of 50 microliters.

The addition of the water-repellent perforated disc fixed to the biopsy causes better floating of the biopsy on the liquid matrix (during deposition in the insert), whereas the floating line passes below the disc. The presence of the disc also enables to delineate with precision the surface area of the biopsy which is in contact with the air. This area is used for performing topical applications. The presence of the perforated disc also enables to avoid the lateral diffusion of solutions or of formulations which are applied to the biopsy, whereas the disc acts as a barrier to the diffusion. The disc finally enables to avoid any contact of the emerged area of the epidermal surface of the biopsy with the mixture of solutions, forming the matrix when the latter is liquid.

Example 3

Implementation of the Method with Different Final Concentrations of Low-Melting Agarose The physicochemical properties of skin fragments held in different solutions of matrices have been compared.

A liquid matrix is prepared from a first solution containing plasma, and of a second solution containing low-melting agarose, whose maximum jellification temperature ranges between 24° C. and 28° C. and whose melting temperature lies above 65.5° C.

In the example where the final proportion of low-melting agarose in the matrix (after contacting the first and the second solution) is 0.25%, the consistency of the matrix is suited for holding the biopsy correctly during road and air transport, without alteration of the biopsy.

Moreover, a solidified matrix comprising 0.25% low-melting agarose preserves a suitable capacity of deformation for holding the biopsy during transport, while preserving the adherence properties of the matrix to the immersed part of the biopsy. The preservation and flexibility properties of the matrix thus prepared are adapted to the realisation of tests with a mechanical effect on the biopsy, as for example an effect mimicking a massage when applying a preparation such as a cream on the skin. Indeed, in such a case, the biopsy remains fixed in the solidified matrix, in spite of the mechanical constraints which may be applied thereto.

The invention claimed is:

1. An ex vivo or in vitro method for ex vivo or in vitro keeping alive and for transporting a natural skin fragment or biopsy, said skin fragment or biopsy having been previously obtained from a mammalian, said method comprising the following steps:
    fixing a ring made of a water-repellent material to the epidermal surface of the natural skin fragment or biopsy, wherein the outer diameter of the ring is greater than the diameter of the epidermal surface of the natural skin fragment or biopsy, and wherein the inner diameter of the ring is smaller than the diameter of the epidermal surface of the natural skin fragment or biopsy;
    after the fixing the ring, laying said natural skin fragment or biopsy in a liquid matrix so that the superficial part of said fragment or biopsy corresponding to the whole epidermis remains above the surface of the liquid matrix such that the dermis underlying the epidermis is completely immersed wherein, said liquid matrix is contained in an insert having a bottom made of a porous membrane, and the insert is disposed in a container or well; and
    solidifying said matrix to trap the immersed portion of said skin fragment or biopsy in said solidified matrix and to cause the solidified matrix to adhere to the lateral walls of the insert and to said porous membrane, wherein the epidermal superficial part of the biopsy remaining above the liquid matrix surface is in contact with the atmospheric air or under a controlled atmosphere partially comprising air.

2. The method of claim 1, wherein said ring is fixed to the epidermal surface of the fragment or of the biopsy using glue, the glue being added to the lower surface of the ring.

3. The method according to claim 1, wherein the skin fragment or biopsy is cylindrical in shape.

4. The method according to claim 1, wherein said insert having the bottom made of a porous membrane, is a nacelle-shaped insert having a diameter ranging between 5 and 40 mm.

5. The method according to claim 1, wherein said porous membrane has a porosity selected between 0.4 and 8 μm.

6. The method according to claim 1, wherein said container, in which said insert has been laid, is a well with a cell culture plate containing 6, 8, 12, 24 or 48 wells.

7. The method according to claim 1, wherein said liquid matrix is a medium containing between 1 mM and 5 mM $Ca^{2+}$ and between 5 and 500 mg/mL ascorbic acid.

8. The method according to claim 1, wherein said liquid matrix is a medium containing between 1 and 2 mM $Ca^{2+}$ and between 5 and 500 mg/mL ascorbic acid.

9. The method according to claim 1, wherein said liquid matrix contained in the insert is capable of solidifying under the action of an increasing or decreasing temperature and/or the addition of a specific compound or composition, wherein and
    the solidification of said matrix is produced by increasing or decreasing the temperature of said matrix and/or by adding said specific compound or composition, wherein the solidification enables the matrix to firmly hold the immersed portion of the skin fragment or biopsy in the insert disposed in the container or well.

10. The method according to claim 1, wherein said liquid matrix is capable of solidifying under the action of an increasing or decreasing temperature and/or the addition of a compound or of a specific composition is selected among any liquid solution capable of solidifying or jellifying under particular conditions compatible with the survival and the culture of the skin fragment or biopsy.

11. The method according to claim 1, wherein said liquid matrix capable of solidifying is a liquid solution derived from a blood plasma treated with an anticoagulant agent having reversible properties, and
    wherein the liquid solution is mixed with an agar-agar or agarose solution.

12. The method of claim 11, wherein said liquid solution derived from plasma is a liquid solution derived from a blood plasma containing from 25% to 60% blood plasma, from 70% to 35% of a physiological solution, from 5% to 12% of 1% $CaCl_2$ salt solution and between 2% and 5% of an anti-fibrinolytic agent.

13. The method according to claim 1, wherein said liquid matrix capable of solidifying is a fibrinogen and thrombin or collagen or blood plasma solution, which is mixed with a gelatin solution comprising synthetic polymeric gels or natural gels selected from the group consisting of agarose gels, starch, polysaccharide gels and their mixtures thereof.

14. The method according to claim 1, wherein said liquid matrix capable of solidifying comprises low-melting point agarose or agar-agar at a final concentration between 0.1% and 5%.

15. The method according to claim 1, wherein said liquid matrix is solidified for a maximum of 8 hours after the skin fragment or biopsy has been laid in the liquid matrix.

16. The method according to claim 1, wherein said liquid matrix contained in the insert does not include any growth factors nor animal and human serum.

17. The method according to claim 1, wherein said liquid matrix contained in the insert is a liquid nutritive matrix capable of solidifying under the action of an increasing or decreasing temperature and/or the addition of a specific compound or composition, the solidification of said matrix being produced by increasing or decreasing the temperature of said matrix and/or by adding said specific compound or composition, and wherein the solidification enables the matrix to hold firmly hold the immersed portion of the skin fragment or biopsy.

18. The method according to claim 1, wherein said liquid matrix is capable of solidifying under the action of an increasing or decreasing temperature and/or the addition of a compound or of a specific composition is selected among any liquid nutritive solution capable of solidifying or jellifying under particular conditions compatible with the survival and the culture of the skin fragment or biopsy.

19. The method according to claim 1, wherein said liquid matrix capable of solidifying is a fibrinogen and thrombin or collagen or blood plasma solution, which is mixed with a gelatin solution comprising synthetic polymeric gels or natural gels selected from the group consisting of agarose or agar-agar gels with low melting points, starch, polysaccharide gels and their mixtures thereof.

20. The method according to claim 1, wherein said liquid matrix capable of solidifying comprises low-melting point agarose or agar-agar at a final concentration between 0.2% and 2%.

21. An ex vivo or in vitro method for preserving or keeping alive a skin fragment or biopsy which can be transported, said method comprising the following steps:
- A) preserving or keeping alive a previously-obtained skin fragment or biopsy capable of being transported, by the method according to claim 1;
- B) transporting said skin fragment or biopsy obtained in step A); and
- C) culturing said skin fragment or biopsy obtained after transport in step B) under adequate culture conditions wherein, the epidermis of said skin fragment or biopsy is above the liquid matrix surface.

\* \* \* \* \*